United States Patent [19]
Chen et al.

[11] Patent Number: 5,185,251
[45] Date of Patent: Feb. 9, 1993

[54] MICROBIAL TRANSFORMATION OF A SUBSTITUTED PYRIDINONE USING ACTINOPLANACETE SP. MA 6559

[75] Inventors: Shieh-Shung T. Chen, Morganville; George Doss, Westfield, both of N.J.

[73] Assignee: Merck & Co., Inc., Rahway, N.J.

[21] Appl. No.: 711,784

[22] Filed: Jun. 7, 1991

[51] Int. Cl.$^5$ .............................................. C12P 17/16
[52] U.S. Cl. ..................................... 435/118; 435/822
[58] Field of Search ................................ 435/118, 822

[56] References Cited

U.S. PATENT DOCUMENTS

| | | | |
|---|---|---|---|
| 3,715,358 | 9/1974 | Witzel et al. | 260/296 R |
| 3,835,143 | 2/1973 | Witzel et al. | 260/294.8 T |
| 3,846,553 | 11/1974 | Shen et al. | 424/263 |
| 4,981,792 | 1/1991 | Chen et al. | 435/119 |
| 4,987,139 | 1/1991 | Chen et al. | 514/321 |
| 4,997,849 | 3/1991 | Petuch et al. | 514/460 |

Primary Examiner—Douglas W. Robinson
Assistant Examiner—S. Saucier
Attorney, Agent, or Firm—Carol S. Quagliato; Charles M. Caruso; Roy D. Meredith

[57] ABSTRACT

Fermentation of the microorganism Actinoplanacete sp. (MA6559), ATTC No. 53771, in the presence of the HIV reverse transcriptase inhibitor

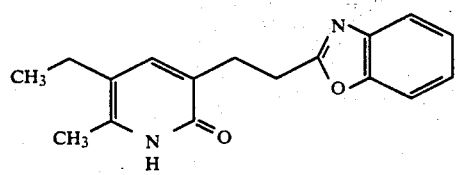

yields 3-[2-(benzoxazol-2-yl)ethyl]-5-(1-hydroxyethyl)-6-methyl-2(1H)-pyridinone and 3-[2-(benzoxazol-2-yl)ethyl]-5-ethyl-6-hydroxymethyl-2(1H)-pyridinone, both of which are useful in the prevention or treatment of infection by HIV and the treatment of AIDS.

3 Claims, No Drawings

MICROBIAL TRANSFORMATION OF A SUBSTITUTED PYRIDINONE USING ACTINOPLANACETE SP. MA 6559

The present invention relates to a novel process for the preparation of compounds (I) and (II)

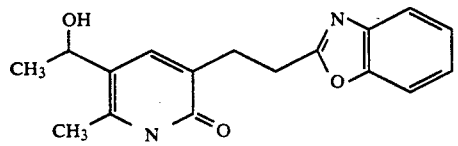

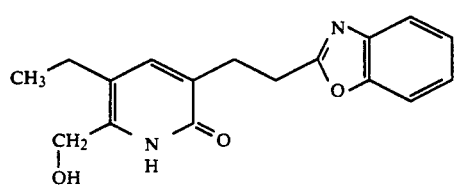

comprising fermentation of compound (III), an inhibitor of the reverse transcriptase encoded by human immunodeficiency virus (HIV)

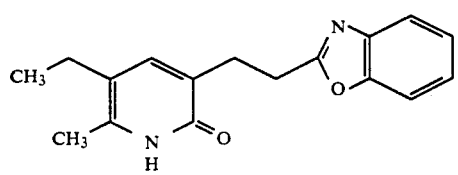

with the microorganism Actinoplanacete sp. (MA6559), ATTCC No. 53771. Compounds (I) and (II) and the pharmaceutically acceptable salts thereof inhibit the reverse transcriptase encoded by HIV and are of value in the prevention of infection by HIV, the treatment of infection by HIV and the treatment of the resulting acquired immune deficiency syndrome (AIDS).

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

The compounds prepared by the process of this invention are inhibitors of HIV reverse transcriptase.

Furthermore, the compounds of the present invention do not require bio-activation to be effective.

SUMMARY OF THE INVENTION

Two HIV reverse transcriptase inhibitors, (I) and (II), are produced from the fermentation of the microorganism Actinoplanacete sp. (MA 6559), ATCC No. 53771, in the presence of substrate compound (III). The biotransformations are accomplished under submerged aerobic conditions in an aqueous carbohydrate medium containing a nitrogen nutrient at a pH of about 7 for a sufficient time to produce compounds (I) and (II).

DETAILED DESCRIPTION OF THE INVENTION AND PREFERRED EMBODIMENTS

The novel process of this invention comprises fermentation of the microorganism Actinoplanacete sp. (MA6559) in the presence of substrate compound (III)

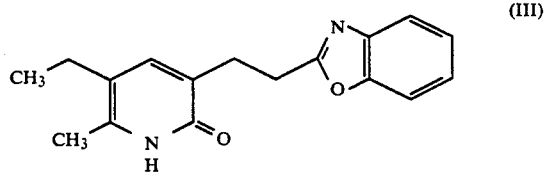

in a nutrient medium, and isolation of the resulting biotransformation products, compounds (I) and (II), in a conventional manner.

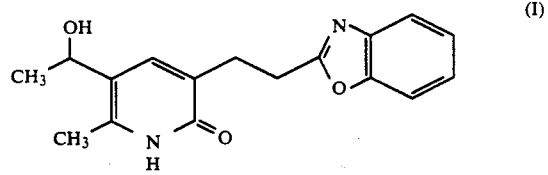

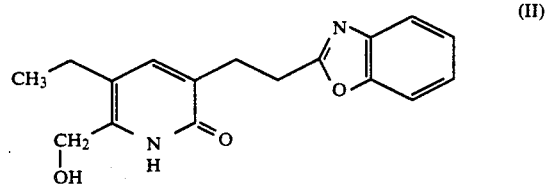

A biologically pure sample of Actinoplanacete sp. (MA6559) was deposited on May 26, 1988 in the permanent culture collection of the American Type Culture Collection, 12301 Parklawn Drive in Rockville, Md., with Accession Number ATCC 53771.

On the basis of the taxonomic analysis performed thus far, the microorganism Actinoplanacete sp. has tentatively been assigned in the order Actinomycetales, in the family Actinoplanacea, and in the genus Streptosporangium, and its characteristics are described below:

Microscopic observations—Culture grows as branched filaments ranging of approximately 6 microns diameter. Spherical to ovoid sporangia are detected on glycerolasparagine agar, oatmeal agar, yeast-malt extract agar and inorganic salts-starch agar. Sporangia range in size from 2.5-44 microns in diameter.

Oat Meal Agar

Vegetative Growth: Reverse is hyaline

Aerial Mass: Moderate, off white, powdery
Soluble Pigment: None.

Glycerol-Asparagine

Vegetative Growth: Obverse is mahogany
Aerial Mycelium: Off white and cottony at periphery turning to dusty rose and powdery at colony center
Soluble Pigment: Very light brown.

Inorganic Salts-Starch Agar

Vegetative Growth: Mahogany
Aerial Mycelium: Off white and cottony at periphery turning to dusty rose and powdery at colony center
Soluble Pigment: Areas of browning around the periphery of growth with slight clearing of starch.

Yeast Extract-Malt Extract Agar

Vegetative Growth: Mahogany to brown black
Aerial Mass: Isolated areas of white, cottony growth against a powdery dusty rose colored mycelial matte
Soluble pigment: Yellow-brown.

Egg Albumin Agar

Vegetative Growth: Pale yellow, flat
Aerial Mass: Sparse, white and cottony limited to periphery of growth
Soluble Pigment: None.

Nutrient Tyrosine Agar

Vegetative Growth: Transparent to pale yellow
Aerial Mass: None
Soluble Pigment: None
Decomposition of tyrosine: Negative.

Skim Milk Agar

Vegetative Growth: Leathery and yellow
Aerial Mass: Sparse, off white and powdery
Soluble Pigment: None
Hydrolysis of casein: Positive.

Tomato Paste Oatmeal Agar

Vegetative Growth: Orange-yellow, rugose
Aerial Mass: Powdery, varying in color from off white to purple-brown.

Gelatin Stabs

Vegetative Growth: Orange yellow
Aerial Mass: None
Soluble Pigment: None
Liquification of gelatin: Positive.

Peptone-Iron-Yeast Extract Agar Slants

Vegetative Growth: Colorless, leathery
Aerial Mass: Moderate, off white, powdery
Soluble Pigment: None
Melanin: Negative
$H_2S$: Negative.

Tryptone Yeast Extract Broth

Soluble Pigment: None.

| Carbohydrate utilization pattern | | | |
|---|---|---|---|
| d-glucose | ++ | l-mannose | − |
| d-arabinose | ++ | d-raffinose | ++ |
| l-arabinose | ++ | l-rhamnose | − |
| d-fructose | ++ | sucrose | +/- |
| l-glucose | +/− | d-xylose | ++ |
| inositol | + | l-xylose | − |
| d-maltose | + | alpha d-lactose | ++ |
| d-mannitol | ++ | beta d-lactose | ++ |
| d-mannose | ++ | | |

Carbon source utilization studies were carried out using Pridham and Gottlieb basal medium supplemented with 1% carbon source. Scoring was graded according to the methods described in "Methods for Characterization of Streptomyces species", IJSB 16: pps 313–340.

In general, compound (I), the 5-(1-hydroxy)ethyl oxidation product, and compound (II), the 6-hydroxymethyl oxidation product, can be produced by culturing (fermenting) the above-described microorganism in the presence of an appropriate concentration of substrate compound (III) in an aqueous nutrient medium containing sources of assimilable carbon and nitrogen, preferably under submerged aerobic conditions (e.g. shaking culture, submerged culture, etc.). An appropriate concentration of the parent compound in the aqueous medium ranges from 0.01 mg/ml to 0.2 mg/ml, preferably 0.05 mg/ml; less than 0.01 mg/ml is inefficient and greater than 0.2 mg/ml can inhibit the culture. The aqueous medium is incubated at a temperature between 26° C. and 29° C., preferably 27° C.; culture growth will be inhibited below this temperature range and culture death will occur above this temperature range. The aqueous medium is incubated for a period of time necessary to complete the oxidative biotransformations as monitored by HPLC, usually for a period of about 24 hours, on a rotary shaker operating at about 220 rpm with a throw of about 2 in. The aqueous medium is maintained at a pH between 6 and 8, preferably about 7, at the initiation and termination (harvest) of the fermentation process. A higher or lower pH will cause the culture to die. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described herein below.

The preferred sources of carbon in the nutrient medium are certain carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form because less pure materials which contain traces of growth factors and considerable quantities of mineral nutrients are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

Substrate compound (III) can be obtained by synthetic organic procedures, as described elsewhere in this application.

Submerged aerobic cultural conditions are preferred for the production of the 5-(1-hydroxy)ethyl and 6-hydroxymethyl oxidation products in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the 5-(1-hydroxy)ethyl and 6-hydroxymethyl oxidation products. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of the 5-(1-hydroxy)ethyl and 6-hydroxymethyl oxidation products and is generally autoclaved to sterilize the medium prior to inoculation. The fermentation medium is generally adjusted to a pH between 6 and 8, preferably about 7, prior to the autoclaving step by suitable addition of an acid or base, preferably in the form of a buffering solution. Temperature of the seed medium is maintained between 26° C. and 29° C., preferably 27° C.; culture growth will be inhibited below this range and culture death will occur above this range. Incubation of the seed medium is usually conducted for a period of about 10 to 30 hours, preferably 24 hours, on a rotary shaker operating at 220 rpm; the length of incubation time may be varied according to fermentation conditions and scales. Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

Preferred culturing/production media for carrying out the fermentation include the following media:

|  | g/l |
| --- | --- |
| Seed Medium A |  |
| Dextrose | 1.0 |
| Dextrin | 10.0 |
| Beef Extract | 3.0 |
| Ardamine pH | 5.0 |
| NZ Amine Type E | 5.0 |
| MgSO$_4$.7H$_2$O | 0.05 |
| K$_2$HPO$_4$ | 0.3 |
| Adjust pH to 7.1 |  |
| Add CaCO$_3$ 0.5 g/l |  |
| Transformation Medium B |  |
| Glucose | 10 |
| Hycase SF | 2 |
| Beef Extract | 1 |
| Corn Steep Liquor | 3 |
| Adjust pH to 7.0 |  |
| Transformation Medium C |  |

-continued

|  | g/l |
| --- | --- |
| Mannitol | 5 |
| Glycerol | 5 |
| Hycase SF | 2 |
| Beef extract | 1 |
| Corn Steep Liquor | 3 |
| Adjust pH t 7.0 |  |

The produced 5-(1-hydroxy)ethyl and 6-hydroxymethyl oxidation products can be recovered from the culture medium by conventional means which are commonly used for the recovery of other known biologically active substances. The 5-(1-hydroxyethyl) and 6-hydroxymethyl oxidation products are found in the cultured mycelium and filtrate, which are obtained by filtering or centrifuging the cultured broth, and accordingly can be isolated and purified from the mycelium and the filtrate by a conventional method such as concentration under reduced pressure, lyophilization, extraction with a conventional solvent, such as methylene chloride and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred recovery method is solvent extraction, particularly using methylene chloride. A preferred purification method involves the use of chromatography, especially HPLC, using a silica gel column and an eluant mixture composed of water and an organic solvent such as methanol, acetonitrile and the like. A preferred eluant is composed of water and acetonitrile and is run through the column in a linear gradient.

Compounds (I) and (II) of the present invention are useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex) both symptomatic and asymptomatic, and actual or potential exposure to HIV. For example, the compounds of this invention are useful in treating infection by HIV after suspected past exposure to HIV by e.g., blood transfusion, organ transplant, accidental needle stick, exchange of body fluids, bites or exposure to patient blood during surgery.

Reverse Transcriptase Assay

The assay measures the incorporation of tritiated deoxyguanosine monophosphate by recombinant HIV reverse transcriptase (HIV RT$_R$) (or other RT) into acid-precipitable cDNA at the Km values of dGTP and poly r(C).oligo d(G)$_{12-18}$. Compounds (I) and (II) of the present invention inhibit this incorporation.

Thirty uL of a reaction mixture containing equal volumes of: 500 mM Tris.HCl (pH 8.2), 300 mM MgCl$_2$, 1200 mM KCl, 10 mM DTT, 400 μg/mL poly r(c).oligo d(G) [prepared by dissolving 1.5 mg (25 U) poly r(C).oligo d(G) in 1.5 ml sterile distilled H$_2$O and diluting to 400 μg/ml], 0.1 μCi/μl [$^3$H] dGTP, 160 μM dGTP, was added to 10 μl sterile distilled H$_2$O, 2.5 μl of potential inhibitor. Ten μL of 3.2 nM purified HIV RT$_R$ were added to start the reaction. The mixture was incubated at 37° C. for 45 minutes.

After incubation was complete, the tubes were cooled in ice for 5 minutes. Ice-cold 13% TCA containing 10 mM NaPP$_i$ (200 μl) was added and the mixture incubated on ice for 30 minutes. The precipitated cDNA was removed by filtration using presoaked glass filters [TCA, NaPP$_i$]. The precipitate was then washed with 1N HCl, 10 mM NaPP$_i$. The filter discs were then counted in a Packard scintillation counter.

Under these conditions [dGTP] and poly r(C).oligo d(G)$_{12-18}$ each are approximately equal to the appropriate Km value. Approximately 5–6,000 cpm of [$^3$H] GMP are incorporated into acid-precipitable material. The RT reaction is concentration- and time-dependent. DMSO (up to 5%) does not affect enzyme activity.

Using the methodology described above, compounds (I) and (II) were evaluated. The calculated IC$_{50}$ of compound (I) was found to be about 18.7 μM and that of compound (II) about 44 nM, thereby demonstrating and confirming the utility of compounds (I) and (II) as effective HIV reverse transcriptase inhibitors.

EXAMPLE 1

Preparation of Substrate Compound (III)

3-[2-(Benzoxazol-2-yl)ethyl]-5-ethyl-6-methyl-2-(1H)-pyridinone

Step A: Preparation of 3-cyano-5-ethyl-6-methyl-2-(1H)-pyridinone

According to the method described in J. Heterocyclic Chem., 24, 351 (1987), a mixture of 2-ethyl-3-oxobutanal, sodium salt (37.5 g, 0.275 mmol), cyanoacetamide (25.2 g, 0.30 mol), aqueous piperidinium acetate (22 mL) [prepared from glacial acetic acid (4.2 mL), water (10 mL) and piperidine (7.2 mL)] in water (775 ml) was refluxed for four hours. Glacial acetic acid (30 ml) was added cautiously (much foaming) as the product precipitated. Upon cooling to room temperature, the product was collected by filtration, washed with cold water and air dried. The product had m.p. of 237°–240° C.

Step B: Preparation of 2-chloro-3-cyano-5-ethyl-6-methylpyridine

3-Cyano-5-ethyl-6-methyl-2-(1H)-pyridinone (22.9 g, .141 mol) and phosphorus pentachloride (33.1 g, 0.159 mol) were intimately mixed and heated at 110°–120° C. for one hour. The liquified solids were poured onto crushed ice and water and the semi-solid was extracted into chloroform. This extract was washed with water, saturated aqueous NaHCO$_3$, dried (Na$_2$SO$_4$), filtered and evaporated. This amber oil was dissolved in hexane and the insoluble material was removed when filtered through a pad of charcoal. Removal of the solvent gave a light yellow oil which solidified (17.7 g). Trituration of this solid with cold hexane yielded pure product, m.p. 63°–64° C.

Step C: Preparation of 2-methoxy-3-cyano-5-ethyl-6-methylpyridine

Sodium metal (3.25 g, .141 mol) was dissolved in dry methanol (100 mL) under a nitrogen atmosphere. When solution was complete, a slurry of 2-chloro-5-ethyl-6-methylpyridine (17.95 g, 99.4 mmol) in dry methanol (70 mL) was added and the reaction was warmed at 60° C. for 15–20 hours. After cooling the reaction mixture, diethyl ether (250 mL) and water (200 mL) were added. The ether layer was separated and washed with water, dried (Na$_2$SO$_4$), filtered and evaporated to give a light yellow solid (17.5 g). This solid was triturated with cold hexane to yield pure product, m.p. 59°–61° C.

Step D: Preparation of 2-methoxy-5-ethyl-6-methylnicotinaldehyde

To a solution of 2-methoxy-3-cyano-5-ethyl-6-methylpyridine (1.0 g, 5.68 mmol) in dry tetrahydrofuran (50 mL) under a nitrogen atmosphere and cooled to −70° C., was added 1.3M diisobutyl aluminum hydride/THF (17.4 mL, 22.7 mmol). The resulting mixture was allowed to warm to room temperature and stir for 15–20 hours. The reaction mixture was acidified with 1N hydrochloric acid and then neutralized with aqueous sodium bicarbonate. Water was then added and the product extracted into diethyl ether. The etheral extract was dried (Na$_2$SO$_4$), filtered and the solvent evaporated. This residue was flash chromatographed on silica gel eluting with 10% diethyl ether/pentane to give the product.

Step E: Preparation of 2-[2(R/S)-hydroxy-2-(2-methoxy-5-ethyl-6-methyl-pyridin-3-yl)ethyl]benzoxazole To a solution of 2-methylbenzoxazole (226 mg, 1.7 mmol) in anhydrous THF (4 mL), cooled to −100° C. under an argon atmosphere, was added 1.6M n-butyllithium/hexane (1.05 mL) slowly over 35 minutes. After 0.5 hour a solution of 2-methoxy-5-ethyl-6-methylnicotinaldehyde (300 mg, 1.7 mmol) in dry THF (1 mL) was added dropwise. The reaction was allowed to warm to room temperature and poured onto crushed ice. This mixture was extracted with diethyl ether. The combined extracts were dried (MgSO$_4$) and the solvent removed to give an oil which was flash chromatographed over silica gel. Elution with ethyl acetate/hexane (1:19) gave analytically pure racemic product, mp 102°–103° C.

Anal. Calcd for C$_{18}$H$_{20}$N$_2$O$_3$. 0.1 H$_2$O: C, 68.81; H, 6.48; N, 8.92. Found: C, 68.80; H, 6.76; N, 8.95.

Step F: Preparation of 3-[2-(benzoxazol-2-yl)ethenyl]-5-ethyl-6-methyl-2-(1H)-pyridinone.

A mixture of 2-[2(R/S)-hydroxy-2-(2-methoxy-5-ethyl-6-methylpyridin-3-yl)ethyl]benzoxazole (72 mg, 0.23 mmol) and pyridine hydrochloride (133 mg, 1.2 mmol), under a nitrogen atmosphere, was placed in a preheated oil bath (165° C.) for 5 minutes. The reaction flask was removed, cooled, and water added to give a solid. This crude product was extracted into chloroform, dried (MgSO$_4$) and the solvent evaporated to yield pure product. Recrystallization from methanol gave analytically pure product, mp 262°–264° C.

Anal. Calcd for C$_{17}$H$_{16}$N$_2$O$_2$: C, 72.83; H, 5.75; N, 10.00. Found: C, 72.93; H, 5.95; N, 9.99.

Step G: Preparation of 3-[2-(benzoxazol-2-yl)ethyl]-5-ethyl-6-methyl-2-(1H)-pyridinone A solution of 80% pure 3-[2-(benzoxazol-2-yl)ethenyl]-5-ethyl-6-methyl-2-(1H)-pyridinone (200 mg) in methanol/ethanol/THF (25 mL, 1:1:1) was hydrogenated at atmospheric pressure over 5% palladium/charcoal for four hours. After filtering off the catalyst, the solvents were evaporated and the residue flash chromatographed over silica gel. Elution with 2% methanol-98% chloroform gave analytically pure product, mp 155°–156.5° C.

Anal. Calcd. for C$_{17}$H$_{18}$N$_2$O$_2$: C, 72.31; H, 6.43; N, 9.92. Found: C, 72.45; H, 6.52; N, 9.99.

EXAMPLE 2

Microorganism and Culture Conditions

A frozen vial (2.0 ml) of culture (MA 6559) ATCC No. 53771 was used to inoculate a 250 ml baffled shake flask containing 50 ml of an autoclaved (sterilized) seed medium consisting of (in units of grams/liter) dextrin 10.0, dextrose 1.0, beef extract 3.0, ardamine pH (Yeast Products, Inc.) 5.0, N-Z Amine type E 5.0, $MgSO_4 \cdot 7H_2O$ 0.05, $K_2HPO_4$ 0.3, and $CaCO_3$ 0.5. The pH of the seed medium was adjusted to 7.1 before autoclaving. The seed was incubated in the seed medium at 27° C. for 24 hours on a rotary shaker operating at 220 rpm. A 2.5 ml aliquot of the resulting seed medium was used to inoculate a 250 ml non-baffled shake flask containing 50 ml of the following previously autoclaved (sterilized) transformation medium B.[1] A DMSO solution of substrate compound (III) was added to the fermentation at zero hour to achieve a final concentration of 0.05 mg/ml. The shake flask contents were subsequently incubated for 24 hours at 27° C. on a rotary shaker operating at 220 rpm. This procedure was followed three times and the three resultant broths were combined for isolation and purification.

1. Transformation medium B consisted of (in grams/liter) glucose 10.0; Hycase SF 2.0; beef extract 1.0; corn steep liquor 3.0; where the pH was adjusted to 7.0 before autoclaving.

Isolation and Purification Procedure for the Broth

The whole broth (150 ml) of transformation media B was extracted three times with methylene chloride (3×150 ml). Methylene chloride extracts were combined, dried over sodium sulfate, and concentrated under vacuum to an oily residue. The residue was dissolved in methanol and subjected to high performance liquid chromatography (HPLC) purification.

HPLC was carried out on Whatman Partisil 10 ODS-3, 9.4 mm×25 cm column at room temperature and monitored at 250 nm. The column was developed at 3 ml/min with linear gradient from $H_2O$—$CH_3CN$, 80:20, to $H_2O$—$CH_3CN$, 20:80 in 30 minutes. The compounds were collected during repeated injections of the above described extract. The fractions at retention time 9.1 and 12.6 minutes were pooled respectively, and evaporated to remove solvents to yield 2.5 mg. of compound (I) characterized as the 5-(1-hydroxy)ethyl oxidation product, and 150 μg of compound (II) characterized as the 6-hydroxymethyl oxidation product, respectively.

EXAMPLE 3

Preparation of Compound (II)

3-[2-(benzoxazol-2-yl)ethyl]-5-ethyl-6-hydroxymethyl-2(1H)-pyridinone

Step A: Preparation of 4-benzyloxy-3-oxo-2-ethylbutanal

A solution of 90% pure 1-(N-morpholino)-1-butene (9.3 g, 60 mmol) and triethylamine (8.4 mL, 60 mmol) in tetrahydrofuran (85 mL), under a nitrogen atmosphere, was warmed to 70° C. and benzyloxyacetyl chloride (9.45 mL, 60 mmol) was added dropwise via syringe. This cloudy yellow solution was warmed for 45 minutes and then cooled to room temperature. An aqueous solution of 10% HCl (75 mL) was added and the two phase mixture was stirred for 1 hour. This mixture was partitioned into methylene chloride and the organic layer was separated, dried ($Na_2SO_4$), filtered and the solvent evaporated to give a yellow oil (14.7 g) which contained 80% desired product. This oil was used directly in the next step.

Step B: Preparation of 3-cyano-5-ethyl-6-benzyloxymethyl-2(1H)-pyridinone

Acetic acid (2.0 mL, 35 mmol) was added to a solution of crude 4-benzyloxy-3-oxo-2-ethylbutanal (6.4 g, ~24 mmol) and malononitrile (2.22 g, 33 mmol) in ethanol (30 mL) followed by dropwise addition of piperidine (2.37 mL, 24 mmol) to give a dark reddish brown solution. After stirring for 14 hours, a copious precipitate formed. This mixture was warmed at 70° C. for 15 hours and then allowed to cool to room temperature. This blackish mixture was diluted with ethanol and the precipitated product was filtered, rinsed with ethanol and diethyl ether to give off-white product with m.p. of 141°–143° C. Additional material was obtained by evaporation of the filtrate. The residue was extracted into chloroform, and after washing the extract with saturated aqueous $NaHCO_3$, filtered through a pad of charcoal. This amber solution was evaporated and the residue triturated with diethyl ether to give additional product.

Step C: Preparation of 2-benzyloxy-3-cyano-5-ethyl-6-benzyloxymethylpyridine

To a partial suspension of 3-cyano-5-ethyl-6-benzyloxymethyl-2(1H)-pyridinone (1.36 g, 5.08 mmol) in dry benzene (20 mL) was added benzyl bromide (0.80 mL, 6.7 mmol) and then silver carbonate (1.43 g, 5.2 mmol). This mixture was covered with aluminum foil and allowed to stir at room temperature. After 24 hours, the reaction was estimated to be ~80% complete. Additional silver carbonate (0.40 g, 1.45 mmol) was added and the mixture was stirred for another 24 hours until complete. The silver salts were removed by filtration, rinsed with benzene and the combined benzene washings were evaporated to give the pure product as an oil.

Step D: Preparation of 2-benzyloxy-5-ethyl-6-benzyloxymethylnicotinaldehyde

To a solution of 2-benzyloxy-3-cyano-5-ethyl-6-benzyloxymethylpyridine (2.57 g, 6.2 mmol) in dry toluene (10 mL), under a nitrogen atmosphere in an ice/acetone bath, was added dropwise a solution of 1.5M diisobutylaluminum hydride/toluene (4.6 mL, 6.9 mmol). After stirring at room temperature for 15 hours, the reaction was cautiously poured into 10% HCl (30 mL), stirred for 0.5 hours and the product extracted into diethyl ether. The ethereal solution was dried, filtered through a pad of charcoal and evaporated to give a pale yellow oil. This oil was further purified by passing a benzene solution through a plug of silica gel to give pure product upon evaporation.

Step E: Preparation of 3-[2-(benzoxazol-2-yl)ethenyl]-5-ethyl-6-benzyloxymethyl-2-benzyloxypyridine To a suspension of [(benzoxazol-2-yl)methyl]triphenylphosphonium chloride (1.77 g, 4.12 mmol) (prepared using substantially the same procedures described in Example 5, but substituting 2-aminophenol and the intermediate thereof for the 2,5-dimethyl-6-aminophenol and its corresponding intermediate used therein), in dry tetrahydrofuran (20 mL), under a nitrogen atmosphere, was added 60% NaH/mineral oil (0.42 g, 10 mmol). After 0.5 hour a solution of 2-benzyloxy-5-ethyl-6-benzyloxymethylnicotinaldehyde (1.44 g, 4.0 mmol) in tetrahydrofuran (10 mL) was added and the reaction mixture was refluxed for 23 hours. The reaction was cooled, neutralized with acetic acid and partitioned between water and chloroform. The chloroform layer was washed with NaHCO₃ solution, dried, filtered through a pad of charcoal and evaporated. This material was dissolved in chloroform and flash chromatographed through silica gel to give pure product as a yellow oil. The product was a mixture of cis and trans olefins.

Step F: Preparation of 3-[2-(benzoxazol-2-yl)ethyl]-5-ethyl-6-benzyloxymethyl-2(1H)-pyridinone A solution of cis/trans 3-[2-(benzoxazol-2-yl)ethenyl]-5-ethyl-6-benzyloxymethyl-2-benzyloxypyridine (1.40 g, 2.94 mmol) in dry tetrahydrofuran (20 mL) and methanol (15 mL) containing 10% Pd on charcoal (215 mg) as a catalyst was hydrogenated at atmospheric pressure for 20 hours. The catalyst was filtered off and the solution evaporated to give a white residue. This residue was triturated with diethyl ether to give pure product with m.p. of 140°–142° C.

Step G: Preparation of 3-[2-(benzoxazol-2-yl)ethyl]-5-ethyl-6-hydroxymethyl-2(1H)-pyridinone A solution of 3-[2-(benzoxazol-2-yl)ethyl]-5-ethyl-6-benzyloxymethyl-2(1H)-pyridinone (198 mg, 0.51 mmol) in dry methylene chloride (6 mL) was cooled in an ice/acetone bath and 1M boron tribromide/hexane (1.5 mL, 1.5 mmol) was added dropwise to give a white precipitate. This suspension was stirred for one hour and then the reaction was quenched by addition of saturated aqueous NaHCO₃ (10 mL). After stirring for 0.5 hours, the product was extracted into CH₂Cl₂, dried, filtered and the solvent evaporated to give a solid. Trituration with diethyl ether gave product as a tan solid. Recrystallization from ethyl acetate afforded a light yellow solid with m.p. of 155°–156° C.

Anal. Calcd. for $C_{17}H_{18}N_2O_3$: C, 68.44; H, 6.08; N, 9.39. Found: C, 68.15; H, 6.03; N, 9.07.

EXAMPLE 4

Preparation of Compound
(I):(+/−)-3-[2-(benzoxazol-2-yl)ethyl]-5-(1-hydroxyethyl)-6-methyl-2(1H)-pyridinone Step A: 2-Benzyloxy-5-acetyl-6-methylpyridin-3-carbonitrile A mixture of 3-cyano-5-acetyl-6-methyl-2(1H)-pyridinone (1.76 g, 0.01 mol) (L. Mosti et al, J. Het. Chem. 22, 1503 (1985)), benzyl bromide (2.12 g, 0.012 mol), silver carbonate (3.06 g, 0.011 mol) in benzene was stirred at room temperature under a nitrogen atmosphere overnight, while protected from light. The following day the mixture was filtered, and the solids washed well with benzene. Evaporation of the filtrate gave the desired intermediate, mp 94°–99° C.

Anal. Calc'd. for $C_{16}H_{14}N_2O_2$, MW 266.299 C, 72.17; H, 5.30; N, 10.52. Found: C, 71.97; H, 5.30; N, 10.19.

Step B: 2-Benzyloxy-5-(1-hydroxyethyl)-6-methylpyridin-3-carbonitrile

Sodium borohydride (0.35 g, 0.0092 mol) was added at room temperature to 2-benzyloxy-5-acetyl-6-methylpyridin-3-carbonitrile (2.44 g, 0.0092 mol) in ethanol (60 mL). After 2 hours chloroform was added plus a few drops of acetic acid. After washing with water and brine, the chloroform solution was evaporated to give product which was not purified further.

Step C: 2-Benzyloxy-5-(1-hydroxyethyl)-6-methylpyridin-3-carboxaldehyde

To a mixture of 2-benzyloxy-5-(1-hydroxyethyl)-6-methylpyridin-3-carbonitrile (1.00 g, 0.0037 mol) in toluene (25 mL), cooled in an ice-acetone bath, was added dropwise diisobutylaluminum hydride (1.5M in toluene) (5.22 mL, 0.0078 mol). After stirring for one hour under nitrogen the mixture was worked up by quenching into a mixture of excess 1N hydrochloric acid and ice. Extraction with chloroform followed by washing with water, saturated sodium bicarbonate solution, and then brine, and evaporation, gave the desired product.

Step D: 3-[2-(benzoxazol-2-yl)ethenyl]-5-(1-hydroxyethyl)-6-methyl-2-benzyloxypyridine Following substantially the same procedure described in Example 3, Step E, but substituting 2-benzyloxy-5-(1-hydroxyethyl)-6-methylpyridin-3-carboxaldehyde for the benzyloxynicotinaldehyde compound used therein, the title compound is obtained.

Step E: (+/−)-3-[2-(Benzoxazol-2-yl)ethyl]-5-(1-hydroxyethyl)-6-methyl-2(1H)-pyridinone Following substantially the same procedure described in Example 3, Step F, but substituting 3-[2-(benzoxazol-2-yl)ethenyl]-5-(1-hydroxyethyl)-6-methyl-2-benzyloxypyridine for the benzyloxypyridine compound used therein, the title compound is obtained.

EXAMPLE 5

Preparation of
[(4,7-dimethylbenzoxazol-2-yl)methyl]triphenylphosphonium chloride Step A: Preparation of 2-chloromethyl-4,7-dimethylbenzoxazole To a solution of 2,5-dimethyl-6-aminophenol (0.67 g, 4.9 mmol) in methylene chloride, solid ethyl 2-chloroiminoacetate hydrochloride (0.85 g, 4.9 mmol) was added. The resultant slurry was stirred at room temperature for 18 hours, then filtered through a plug of diatomaceous earth and concentrated under reduced pressure (15 torr). The solid residue was subjected to column chromatography on silica gel (50 g, eluted with 1% methanol in chloroform). Collection and concentration of appropriate fractions yielded the title benzoxazole.

Step B: Preparation of [(4,7-dimethylbenzoxazol-2-yl)methyl]-triphenylphosphonium chloride The product of Step A above was heated with an equimolar amount of triphenylphosphine in refluxing toluene for 15–25 hours to obtain the title compound.

EXAMPLE 6

Characterization

The structures of the two biotransformation products, compounds (I) and (II), were determined by proton NMR run in CD₃OD. Compound (II) was shown to result from hydroxylation of the methyl group, and compound (I) from hydroxylation at —CH₂— of the ethyl side chain.

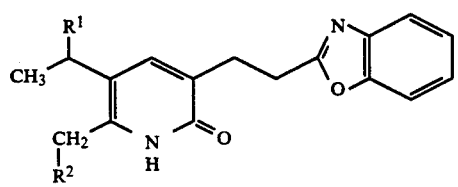

| Compound | $R^1$ | $R^2$ |
|---|---|---|
| (I) | OH | H |
| (II) | H | OH |

-continued

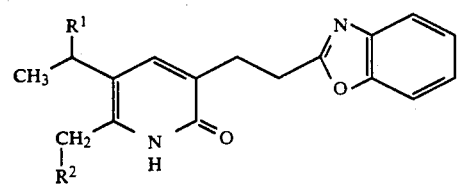

| Compound | R¹ | R² |
|---|---|---|
| (III) | H | H |

Hydroxylation of the methyl group in (II) was indicated by the disappearance of the methyl singlet near 2.2 ppm of substrate compound (III) and the appearance instead of a new singlet at ~4.45 ppm ascribable to the $CH_2OH$ protons.

Hydroxylation of C-1 of the ethyl side chain in compound (I) was evident from the appearance of the terminal methyl group as a doublet (rather than a triplet), and the appearance of a CHOH quartet near 4.8 ppm instead of the methylene quartet at ~2.25 ppm in the parent compound.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process for the preparation of a compound represented by formula (I) or (II)

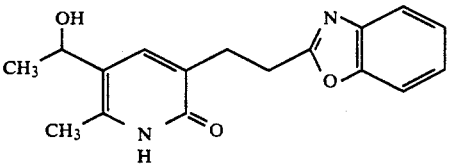

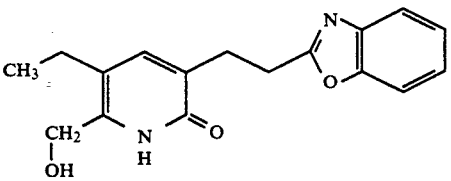

comprising the steps of culturing a microorganism Actinoplanacete sp. (MA 6559) (ATCC 53771) in a nutrient medium containing assimilable sources of nitrogen and carbon and substrate compound (III)

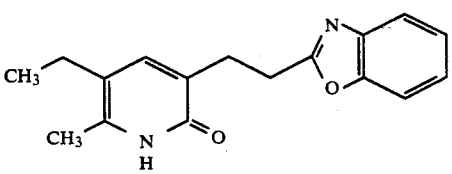

under aerobic conditions until a substantial amount of the compounds are produced and isolating the compounds so produced.

2. The process of claim 1 wherein the temperature is 26°–29° C.

3. The process of claim 2 wherein the temperature is 27° C.

* * * * *